United States Patent
Hasegawa et al.

(10) Patent No.: US 7,884,337 B2
(45) Date of Patent: Feb. 8, 2011

(54) FLUORESCENT MICROSCOPE AND FLUORESCENT CORRELATION SPECTRAL ANALYSIS DEVICE

(75) Inventors: Yutaka Hasegawa, Hamamatsu (JP); Yasunori Igasaki, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 591 days.

(21) Appl. No.: 11/661,326

(22) PCT Filed: Sep. 2, 2005

(86) PCT No.: PCT/JP2005/016131
§ 371 (c)(1),
(2), (4) Date: Mar. 5, 2007

(87) PCT Pub. No.: WO2006/028020
PCT Pub. Date: Mar. 16, 2006

(65) Prior Publication Data
US 2007/0262264 A1    Nov. 15, 2007

(30) Foreign Application Priority Data
Sep. 6, 2004    (JP) .............................. 2004-258927

(51) Int. Cl.
| | |
|---|---|
| *G01J 1/58* | (2006.01) |
| *G01J 3/433* | (2006.01) |
| *G01N 21/64* | (2006.01) |
| *G21K 5/00* | (2006.01) |
| *G02B 21/06* | (2006.01) |

(52) U.S. Cl. .................. 250/458.1; 356/302; 356/303; 356/323; 359/368; 359/385

(58) Field of Classification Search ............ 250/458.1, 250/459.1; 356/323, 368, 302, 303; 359/237, 359/279, 368, 385; 600/109, 310, 312
See application file for complete search history.

(56) References Cited

U.S. PATENT DOCUMENTS

| | | | | |
|---|---|---|---|---|
| 6,483,641 | B1* | 11/2002 | MacAulay | ............... 359/385 |
| 6,515,289 | B1* | 2/2003 | Kask | ............... 250/459.1 |
| 6,573,953 | B1* | 6/2003 | Igasaki et al. | ............... 349/25 |
| 2004/0114138 | A1* | 6/2004 | Hell | ............... 356/318 |
| 2007/0206278 | A1* | 9/2007 | Dyba et al. | ............... 359/385 |

FOREIGN PATENT DOCUMENTS

| | | |
|---|---|---|
| JP | 8-122650 | 3/1996 |
| JP | 2001-305058 | 10/2001 |
| JP | 2003-121749 | 4/2003 |

(Continued)

*Primary Examiner*—David P Porta
*Assistant Examiner*—Jessica L Eley
(74) *Attorney, Agent, or Firm*—Drinker Biddle & Reath LLP

(57) ABSTRACT

A fluorescence microscope 11 includes an objective lens 101, a dichroic mirror 102, a half mirror 105, a mirror 106, a laser light source 111, an ND filter 112, a beam expander 113, a mirror 114, a spatial light modulator 115, a lens 131, a band pass filter 132, a spatial light modulator 133, and a detector, etc. The spatial light modulator 115 can vary its spatial light modulation, and can set the number, positions, and shapes of regions to be irradiated with excitation light in the determined specimen 1 by irradiating the determined specimen 1 with spatially modulated excitation light via the subsequent optical system.

10 Claims, 12 Drawing Sheets

FOREIGN PATENT DOCUMENTS

| | | |
|---|---|---|
| JP | 2003-167198 | 6/2003 |
| JP | 2003-185928 | 7/2003 |
| JP | 3517241 | 1/2004 |
| JP | 2004-191251 | 7/2004 |
| WO | 2004/017069 | 2/2004 |

* cited by examiner

Fig.11
(a)
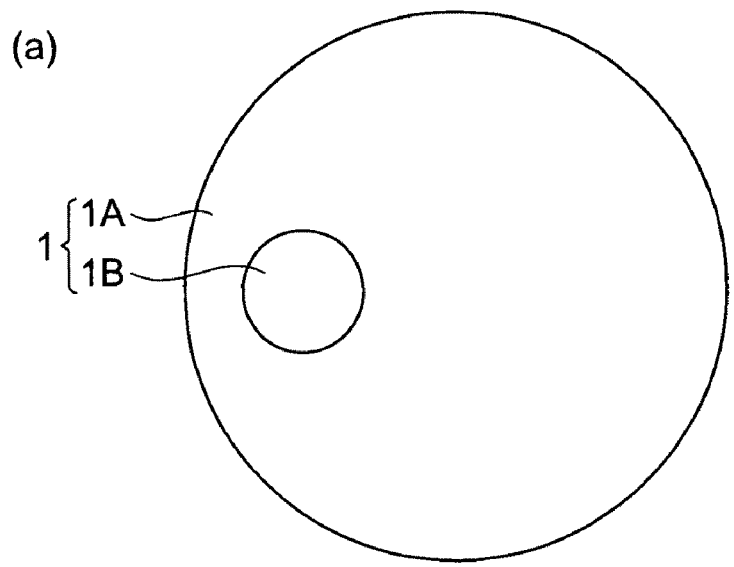
(b)
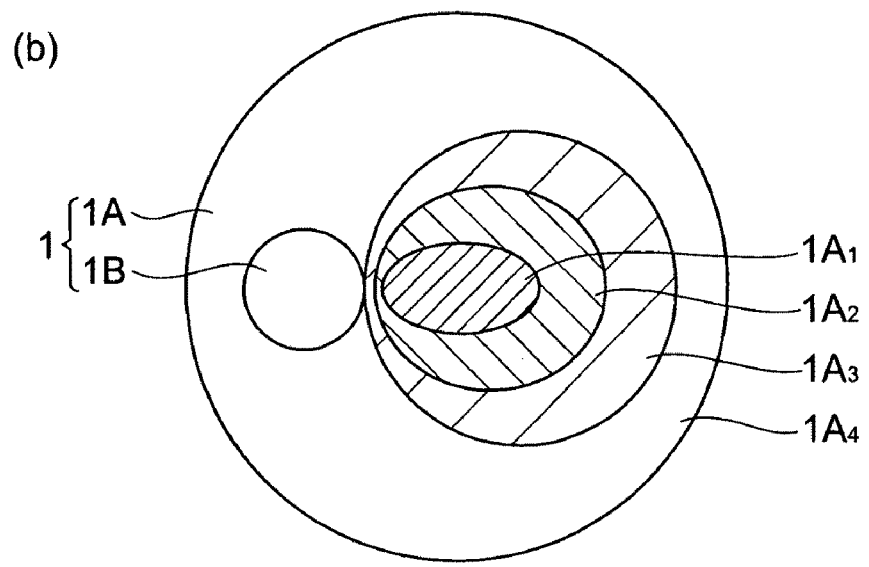

US 7,884,337 B2

FLUORESCENT MICROSCOPE AND FLUORESCENT CORRELATION SPECTRAL ANALYSIS DEVICE

TECHNICAL FIELD

The present invention relates to a fluorescence correlation spectroscopy analysis device which determines a translational diffusion constant, etc., of a fluorescent material based on temporal fluctuation of the intensity of fluorescence emitted from the fluorescent material in a determined specimen, and a fluorescence microscope to be preferably used in this fluorescence correlation spectroscopy analysis device.

BACKGROUND ART

According to the fluorescence correlation spectroscopy (FCS), a micro region in a determined specimen of a solution containing a fluorescent material at an extremely low concentration is irradiated with excitation light, the intensity of fluorescence generated in the micro excitation light irradiation region is detected, an autocorrelation function of a change over time in fluorescence intensity is calculated, and this autocorrelation function is analyzed to determine translational diffusion motion of the fluorescent material in the determined specimen (for example, refer to Patent Document 1).

A fluorescence correlation spectroscopy analysis device which analyzes a fluorescent material in a determined specimen by using this fluorescence correlation spectroscopy includes a confocal fluorescence microscope for excitation light irradiation and fluorescence detection and an analyzer which calculates and analyzes an autocorrelation function based on the intensity of fluorescence detected by the fluorescence microscope.

In Patent Document 1, multi-array detection using the fluorescence correlation spectroscopy is referred to. The multi-array detection referred to in this document is considered to detect fluorescence generated in each of a plurality of excitation light irradiation regions irradiated with excitation light and calculate and analyze an autocorrelation function for each excitation light irradiation region.

If simultaneous or successive determination of a plurality of excitation light irradiation regions is possible by means of fluorescence correlation spectroscopy as described in this document, for example, observation of interaction between molecules of protein or the like inside a cell as a determined specimen is considered to be allowed.

Patent Document 1: Japanese Examined Patent Publication No. 3517241

DISCLOSURE OF THE INVENTION

Problem to be Solved by the Invention

To determine a plurality of excitation light irradiation regions inside a cell as a determined specimen, these excitation light irradiation regions to be determined are not always present on a predetermined plane perpendicular to the excitation light incidence direction, and may be present at positions different in the excitation light incidence direction, and in some cases, it is desired to three-dimensionally determine the inside of a cell. The transmissivity and refractive index inside the cell are not uniform, and unevenness in excitation light irradiation intensity and aberrations may come into question.

However, the excitation light irradiating optical system in conventional devices including the device described in Patent Document 1 cannot be applied when a plurality of excitation light irradiation regions are present at positions different in the excitation light irradiation direction and when the transmissivity and the refractive index are not uniform. Patent Document 1 does not disclose or suggest a construction of an excitation light irradiating optical system for irradiating a plurality of excitation light irradiation regions with excitation light and a construction of a fluorescence detecting optical system for detecting fluorescence generated in each of the excitation light irradiation regions.

The present invention was made for solving the problem, and an object thereof is to provide a fluorescence microscope and a fluorescence correlation spectroscopy analysis device including a excitation light irradiating optical system to be preferably used for simultaneously or successively determining a plurality of excitation light irradiation regions.

Means for Solving the Problem

To solve the problem, a fluorescence microscope according to the invention which irradiates a determined specimen with excitation light and detects fluorescence generated accordingly therein, includes: (1) an excitation light source which outputs excitation light, (2) an excitation light irradiating optical system which has a spatial light modulator that spatially modulates excitation light outputted from the excitation light source and irradiates the determined specimen with the excitation light spatially modulated by this spatial light modulator, (3) a fluorescence detecting optical system which receives fluorescence generated in a region irradiated with the excitation light by the excitation light irradiating optical system and forms an image on the imaging surface, and has selective output means for selectively outputting fluorescence made incident on a specific region of the imaging surface, and (4) a detector which detects an intensity of fluorescence outputted from the selective output means.

A fluorescence correlation spectroscopy analysis device according to the invention includes the fluorescence microscope according to the invention and an analyzer which calculates an autocorrelation function of a change over time in intensity of fluorescence detected by the detector of the fluorescence microscope.

According to the invention, excitation light outputted from the excitation light source is spatially modulated by the spatial light modulator included in the excitation light irradiating optical system and irradiated onto a determined specimen. Fluorescence generated in a region irradiated with the excitation light by the excitation light irradiating optical system is taken an image by the fluorescence detecting optical system, and fluorescence inputted into a specific region of the imaging surface is selectively outputted by the selective output means. The intensity of the fluorescence outputted from the selective output means is detected by the detector. Then, by the analyzer, an autocorrelation function of a change over time in intensity of the fluorescence detected by the detector is calculated.

Herein, the spatial light modulator included in the excitation light irradiating optical system is preferably a phase modulation type. The selective output means included in the fluorescence detecting optical system is preferably a spatial light modulator, and more preferably, an intensity modulation type spatial light modulator. Preferably, the fluorescence microscope of the invention further includes imaging means for imaging a determined specimen.

Preferably, the fluorescence microscope according to the present invention, in which (1) the excitation light source outputs first excitation light and second excitation light that are different in wavelength from each other, (2) exclusive spatial light modulators are provided for the respective first excitation light and the second excitation light as the spatial light modulator of the excitation light irradiating optical system, and the excitation light irradiating optical system irradiates the determined specimen with the spatially modulated first excitation light and second excitation light in the same light path, (3) the fluorescence detecting optical system has a separator which separates first fluorescence generated in a region irradiated with the first excitation light in the determined specimen and second fluorescence generated in a region irradiated with the second excitation light from each other, and has the selective output means separately for each of the first fluorescence and the second fluorescence; and (4) the detector detects intensities of the first fluorescence and the second fluorescence outputted from the selective output means.

In this case, the fluorescence correlation spectroscopy analysis device of the invention includes the fluorescence microscope according to the invention and an analyzer which calculates a cross correlation function of changes over time in intensity of first fluorescence and second fluorescence detected by the detector of the fluorescence microscope.

In this case, the respective first excitation light and second excitation light outputted from the excitation light source are spatially modulated by the spatial light modulator included in the excitation light irradiating optical system so as to have the same light path and irradiated onto the determined specimen. First fluorescence generated in an excitation light irradiation region irradiated with the first excitation light and second fluorescence generated in an excitation light irradiation region irradiated with the second excitation light are separated from each other and taken an image by the fluorescence detecting optical system, and fluorescences inputted in specific regions of the imaging surfaces are selectively outputted by the selective output means. The intensities of the first fluorescence and second fluorescence outputted from the selective output means are detected by the detector. Then, by the analyzer, a cross correlation function of changes over time in intensity of the first fluorescence and the second fluorescence is calculated.

EFFECTS OF THE INVENTION

The fluorescence microscope and fluorescence correlation spectroscopy analysis device according to the invention can simultaneously or successively determine a plurality of excitation light irradiation regions by fluorescence correlation spectroscopy.

BRIEF DESCRIPTION OF THE DRAWINGS

FIG. 11 are drawings showing images of the determined specimen 1 taken as an image at Step S3 and fluorescence detection results of the determined specimen 1 obtained at Step S8.

DESCRIPTION OF REFERENCE NUMERALS

Figure 1:
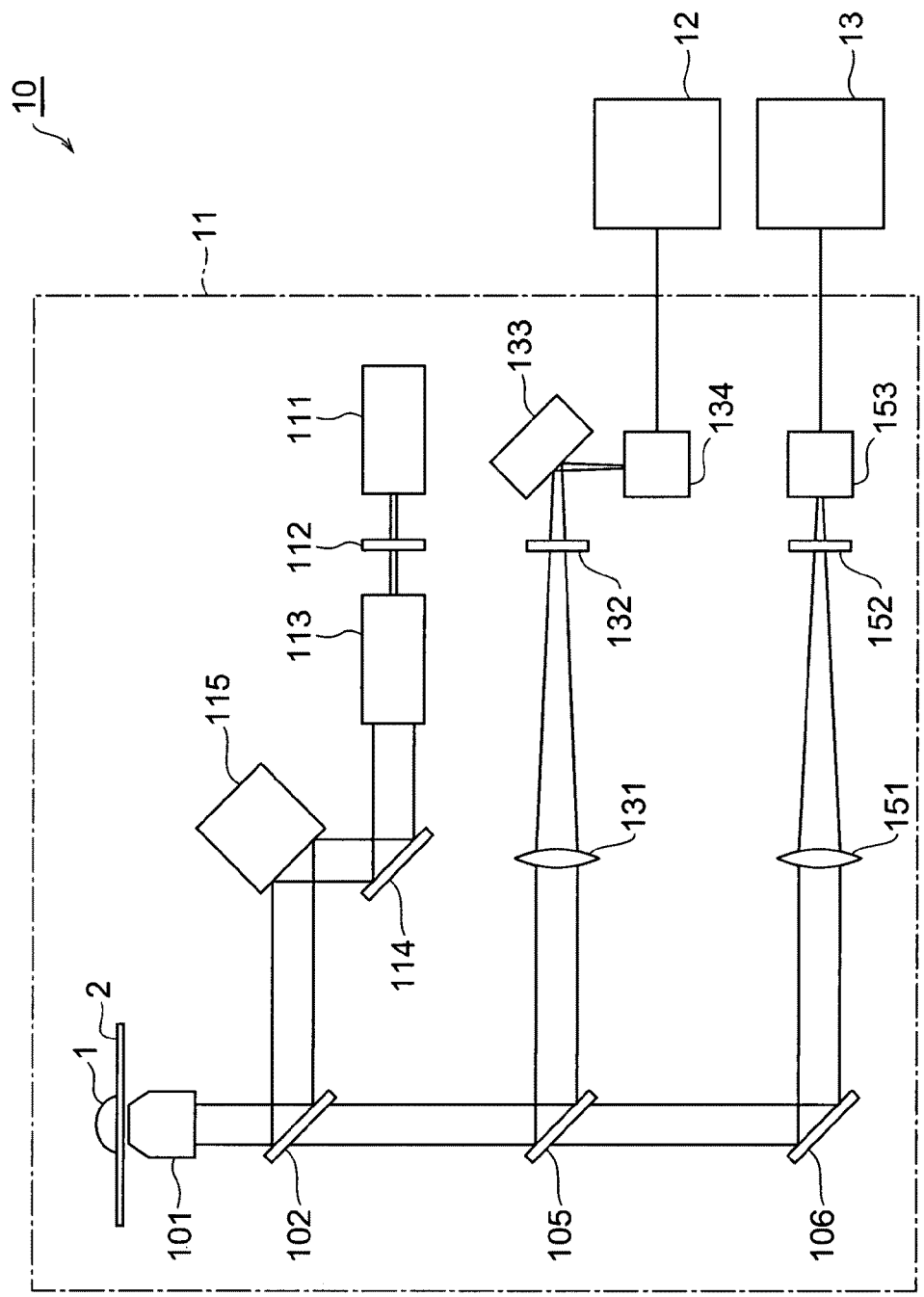
FIG. 1 is a construction diagram of a fluorescence correlation spectroscopy analysis device 1 according to a first embodiment of the invention.

1 Determined specimen
2 Transparent plate
10 Fluorescence correlation spectroscopy analysis device
11 Fluorescence microscope
12 Analyzer
13 Display
20 Fluorescence correlation spectroscopy analysis device
21 Fluorescence microscope
22 Analyzer
101 Objective lens
102-104 Dichroic mirror
105 Half mirror
106, 107 Mirror
111 Laser light source
112 ND filter
113 Beam expander
114 Mirror
115 Spatial light modulator
121 Laser light source
122 ND filter
123 Beam expander
124 Mirror
125 Spatial light modulator
131 Lens
132 Band pass filter
133 Spatial light modulator
134 Detector
141 Lens
142 Band pass filter
143 Spatial light modulator
144 Detector
151 Lens
152 Band pass filter
153 CCD

BEST MODES FOR CARRYING OUT THE INVENTION

Hereinafter, preferred embodiments of the invention will be described in detail with reference to the accompanying drawings. For easy understanding of the description, the components identical in the drawings are attached with the same reference numerals whenever possible, and overlapping description will be omitted.

First Embodiment

First, a first embodiment of the fluorescence microscope and fluorescence correlation spectroscopy analysis device of the invention will be described. FIG. 1 is a construction diagram of the fluorescence correlation spectroscopy analysis device 10 according to the first embodiment. The fluorescence microscope spectroscopy analysis device 10 shown in this drawing includes a fluorescence microscope 11, an analyzer 12, and a display 13, and detects fluorescence generated in a determined specimen 1 by irradiating the determined specimen 1 placed on a transparent plate 2 with excitation light.

The fluorescence microscope 11 includes an objective lens 101, a dichroic mirror 102, a half mirror 105, a mirror 106, a laser light source 111, an ND filter 112, a beam expander 113, a mirror 114, a spatial light modulator 115, a lens 131, a band pass filter 132, a spatial light modulator 133, a detector 134, a lens 151, a band pass filter 152, and a CCD (Charge Coupled Device) 153.

The optical system from the laser light source 111 to the determined specimen 1 forms an excitation light irradiating optical system for irradiating the determined specimen 1 with excitation light outputted from the laser light source 111. The optical system from the determined specimen 1 to the detector 134 forms a fluorescence detecting optical system which guides fluorescence generated in the determined specimen 1 to the detector 134. The optical system from the determined specimen 1 to the CCD 153 forms an imaging optical system and imaging means for imaging the determined specimen 1.

The laser light source (excitation light source) 111 outputs excitation light with a wavelength capable of exciting a fluorescent material contained in the determined specimen 1. The ND filter 112 adjusts the intensity of the excitation light outputted from the laser light source 111 and outputs it. The beam expander 113 receives an input of the excitation light outputted from the ND filter 112, enlarges the light beam diameter of the excitation light to an appropriate diameter, and collimates the light, and then outputs it.

The spatial light modulator 115 receives an input of excitation light that was outputted from the beam expander 113 and reflected by the mirror 114, spatially modulates it with respect to the excitation light, and outputs the spatially modulated excitation light. The spatial light modulator 115 is variable in spatial modulation, and can set the number, positions, and shapes of regions to be irradiated with excitation light in the determined specimen 1 by irradiating the determined specimen 1 with spatially modulated excitation light via the subsequent optical system, and can solve the problem in unevenness in intensity of excitation light irradiation and aberrations.

This spatial light modulator 115 may be a transmission type or a reflection type. The spatial light modulator 115 may be an amplitude modulation type or a phase modulation type, or may modulate both the amplitude and phase. However, in terms of use efficiency of excitation light, it is preferable that the spatial light modulator 115 is a phase modulation type. For example, as the spatial light modulator 115, one including micro pixels containing liquid crystals two-dimensionally aligned on a plane is used.

The dichroic mirror 102 reflects excitation light outputted from the spatial light modulator 115 and makes it incident on the objective lens 101, and transmits fluorescence outputted from the objective lens 101. The objective lens 101 inputs excitation light reflected by the dichroic mirror 102 and irradiates a predetermined region (excitation light irradiation region) in the determined specimen 1 with the excitation light. The objective lens 101 inputs fluorescence generated in the excitation light irradiation region and outputs the fluorescence to the dichroic mirror 102.

The half mirror 105 receives an input of light that was outputted from the objective lens 101 and transmitted through the dichroic mirror 102, branches the light into two directions by reflecting a part of the light and transmitting the remainder, and outputs the reflected light to the lens 131 and outputs the transmitted light to the mirror 106. A detachable mirror may be used instead of the half mirror 105. The lens 131 inputs fluorescence reflected by the half mirror 105 to form an image of the fluorescence generated in the excitation light irradiation region in the determined specimen 1 on the spatial light modulator 133 in conjunction with the objective lens 101. The band pass filter 132 is provided on a light path between the lens 131 and the spatial light modulator 133, and selectively transmits the fluorescence, and on the other hand, blocks scatter components of the excitation light.

The spatial light modulator 133 serves as selective output means for selectively outputting fluorescence made incident on a specific region of the imaging surface of the fluorescence taken an image by the objective lens 101 and the lens 131. It is also possible that a mask with an aperture is used instead of the spatial light modulator 133 and the fluorescence image is positioned at the aperture (specific region). However, it is preferable that the position of the specific region is variable, so that it is preferable that the number, positions, and shapes of specific regions from which fluorescence is selectively outputted are variable. Thereby, an equivalent confocal optical system can be realized.

The spatial light modulator 133 may be a transmission type or a reflection type. The spatial light modulator 133 may be an amplitude modulation type or a phase modulation type, or may modulate both the amplitude and phase. However, the spatial modulator 133 in the detecting optical system does not need various condition controls in comparison with the spatial light modulator 115 in the excitation light irradiating optical system, so that an intensity modulation type is preferable in terms of cost. For example, as the spatial light modulator 133, a digital micromirror device (DMD) made by Texas Instruments Inc. is preferably used.

The detector 134 detects an intensity of fluorescence which was outputted from the spatial light modulator 133 and reached the detector. As this detector 134, a photomultiplier or an avalanche photodiode are preferably used. The analyzer 12 stores a change I(t) over time in intensity of fluorescence detected by the detector 134, and calculates an autocorrelation function G(τ) from I(t) (see the following expression (1)). Then, based on this autocorrelation function G(τ), a translational diffusion constant, etc., of a fluorescent material in the excitation light irradiation region in the determined specimen 1 can be calculated. Herein, t indicates a time variable, and τ indicates a variable showing correlation time.

[Numerical expression 1]

$$G(\tau) = \frac{\langle I(t) \cdot I(t+\tau) \rangle}{\langle I(t) \rangle^2} \quad (1)$$

The mirror 106 reflects light transmitted through the half mirror 105 toward the lens 151. The lens 151 receives an input of light reflected by the mirror 106 and forms an image of light generated in the excitation light irradiation region in the determined specimen 1 on the imaging surface of the CCD 153 in conjunction with the objective lens 101. The band pass filter 152 is provided on a light path between the lens 151 and the CCD 153, and transmits fluorescence, and on the other hand, blocks scatter components of excitation light. The CCD 153 images the image formed on the imaging surface. The display 13 displays the image taken an image by the CCD 153. The display 13 is also preferable for displaying results of analysis made by the analyzer 12.

Figure 2:
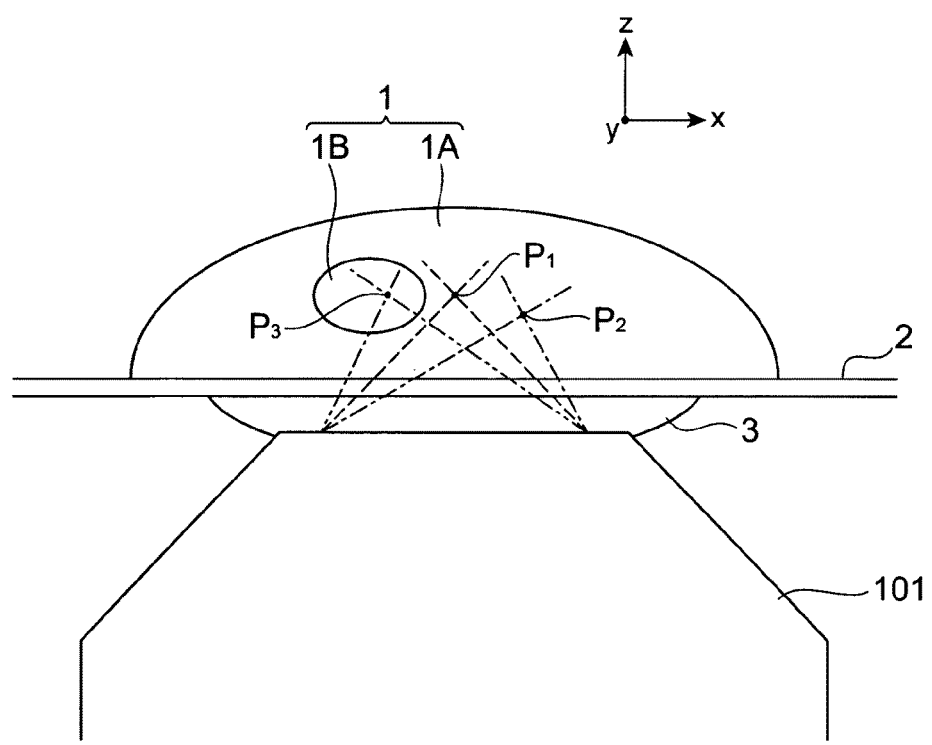
FIG. 2 is an enlarged view of an objective lens 101 and a determined specimen 1.

FIG. 2 is an enlarged view of the objective lens 101 and the determined specimen 1. As the objective lens 101, a water-immersion object is used, and in the light path between the objective lens 101 and the transparent plate 2, water 3 is filled. The transparent plate 2 is a plate made of a nonluminescent material with a high transmissivity for both excitation light and fluorescence, and for example, a cover glass made of silica glass is preferably used. The determined specimen 1 is placed on the transparent plate 2.

The number, positions, and shapes of excitation light irradiation regions in the determined specimen 1 are set according to spatial modulation of excitation light in the spatial light modulator 115 in the excitation light irradiating optical system. This is because excitation light whose wavefront was adjusted by spatial modulation by the spatial light modulator 115 is influenced by an optical transfer function of the optical system from the spatial light modulator 115 to the determined specimen 1 and then irradiated onto the determined specimen 1. That is, the spatial modulation of excitation light in the spatial light modulator 115 is defined based on the optical transfer function of the optical system from the spatial light modulator 115 to the determined specimen 1 and a position of a desired excitation light irradiation region in the determined specimen. The positions of the respective excitation light irradiation regions can be set not only in the directions (x direction and y direction) perpendicular to the optical axis of the objective lens 101 but also in the direction (z direction) parallel to the optical axis of the objective lens 101. The plurality of excitation light irradiation regions can be simultaneously or successively irradiated with excitation light.

In FIG. 2, the determined specimen 1 has an observation region 1A and an observation region 1B. The observation region 1A and the observation region 1B are different from each other in refractive index or transmissivity. In addition, three excitation light irradiation regions $P_1$ through $P_3$ are shown. The excitation light irradiation regions $P_1$ and $P_2$ are positioned within the observation region 1A, and the excitation light irradiation region $P_3$ is positioned within the observation region 1B.

Figure 3:
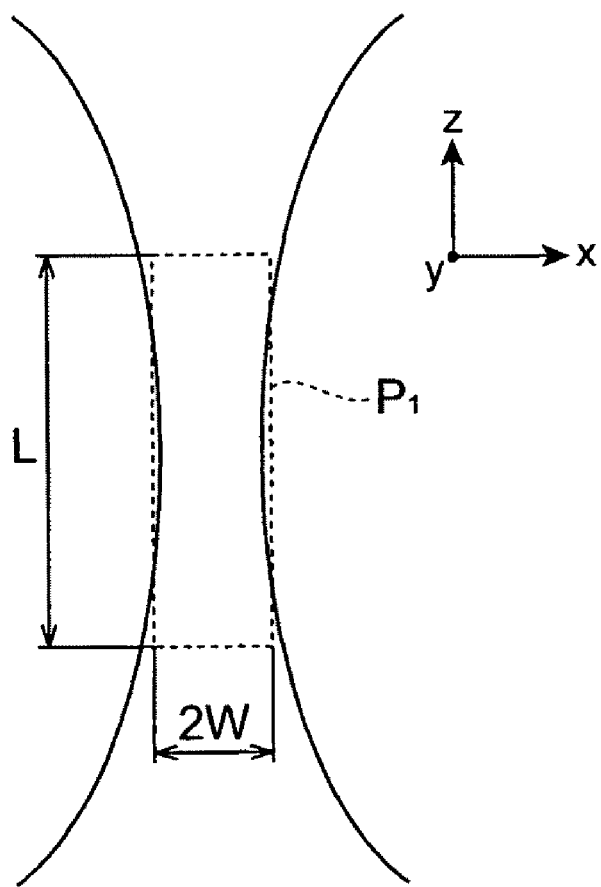
FIG. 3 is an enlarged view of an excitation light irradiation region in the determined specimen 1.

FIG. 3 is an enlarged view of the excitation light irradiation region in the determined specimen 1. Generally, when light with a certain definite light beam diameter is condensed by a condenser lens, a light beam at the condensed position has a gaussian intensity distribution in the diameter direction and a beam waist with a radius w. In the fluorescence correlation spectroscopy, a columnar region with a radius w and a length L is considered as the excitation light irradiation region, and the molecule counts of a fluorescent material is present in this excitation light irradiation region is set to several. Then, due to entrance and exit of the fluorescent material into and from the excitation light irradiation region, the molecule counts of the fluorescent material present in the excitation light irradiation region temporally fluctuate, and the intensity of fluorescence generated from the excitation light irradiation region also temporally fluctuates, so that based on an autocorrelation function $G(\tau)$ showing temporal fluctuation of the fluorescence intensity, the translational diffusion constant or the like of the fluorescent material in the excitation light irradiation region can be calculated.

FIG. 4 to FIG. 9 are drawings showing examples of spatial phase modulation of excitation light in the spatial light modulator 115. FIG. 4A, FIG. 5A, FIG. 6A, FIG. 7, FIG. 8, and FIG. 9 show phase modulations of excitation light for each pixel in the spatial light modulator 115 by shading, respectively, and for example, 256 phase values of equal divisions from 0 to $2\pi$ are indicated as shades in 256 grayscale. FIG. 4B, FIG. 5B, and FIG. 6B show the positions of the excitation light irradiation regions in the determined specimen 1 in the field of objective lens 101 by black points.

Figure 4:
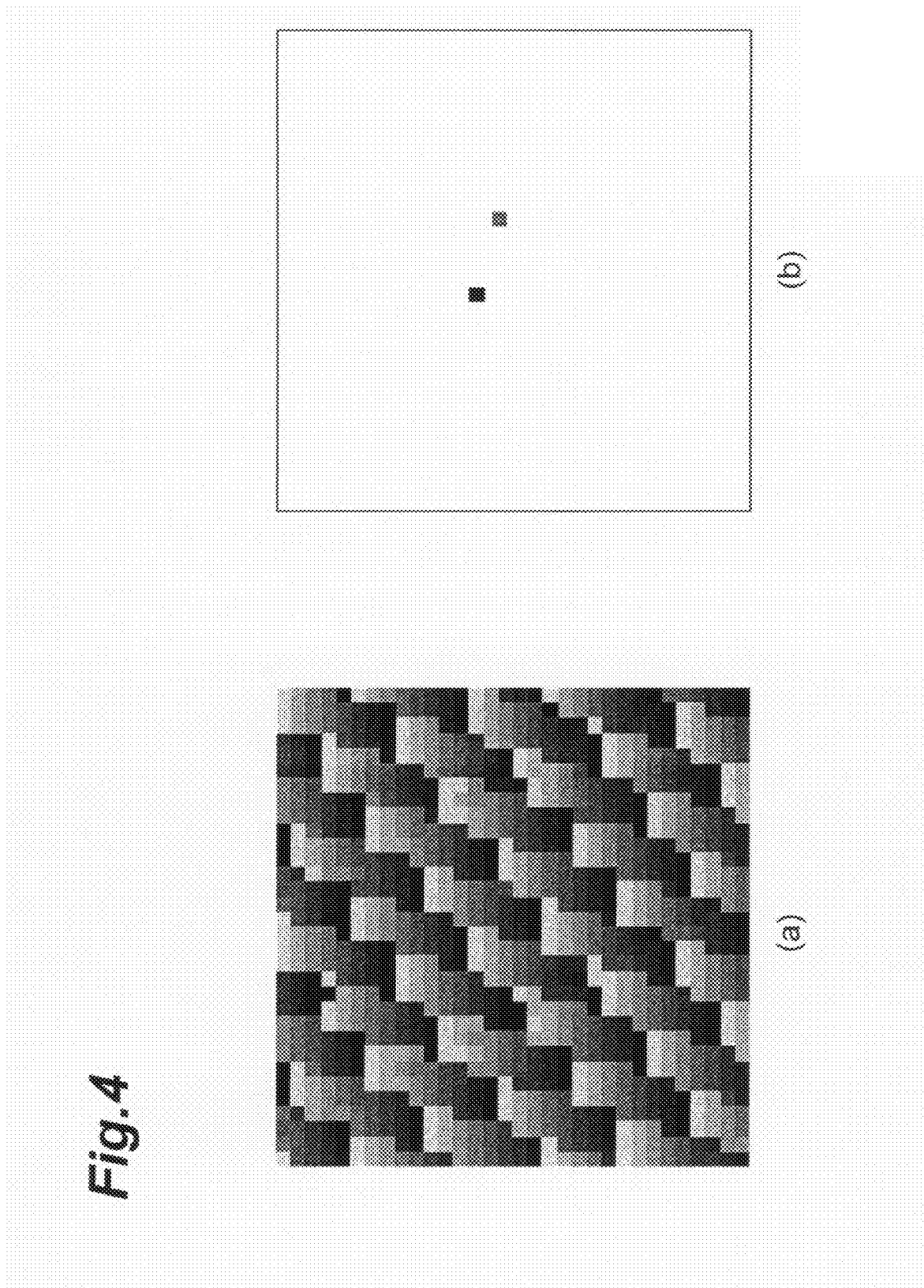
FIG. 4 are drawings showing a first example of spatial phase modulation of excitation light in a spatial light modulator 115.

In the first example shown in FIGS. 4, a two-dimensional phase grating as shown in FIG. 4A is formed in the spatial light modulator 115, and according to this, two excitation light irradiation regions shown in FIG. 4B are formed in the determined specimen 1. In FIG. 4B, the excitation light intensity in the left excitation light irradiation region is twice the excitation light intensity in the right excitation light irradiation region.

Figure 5:
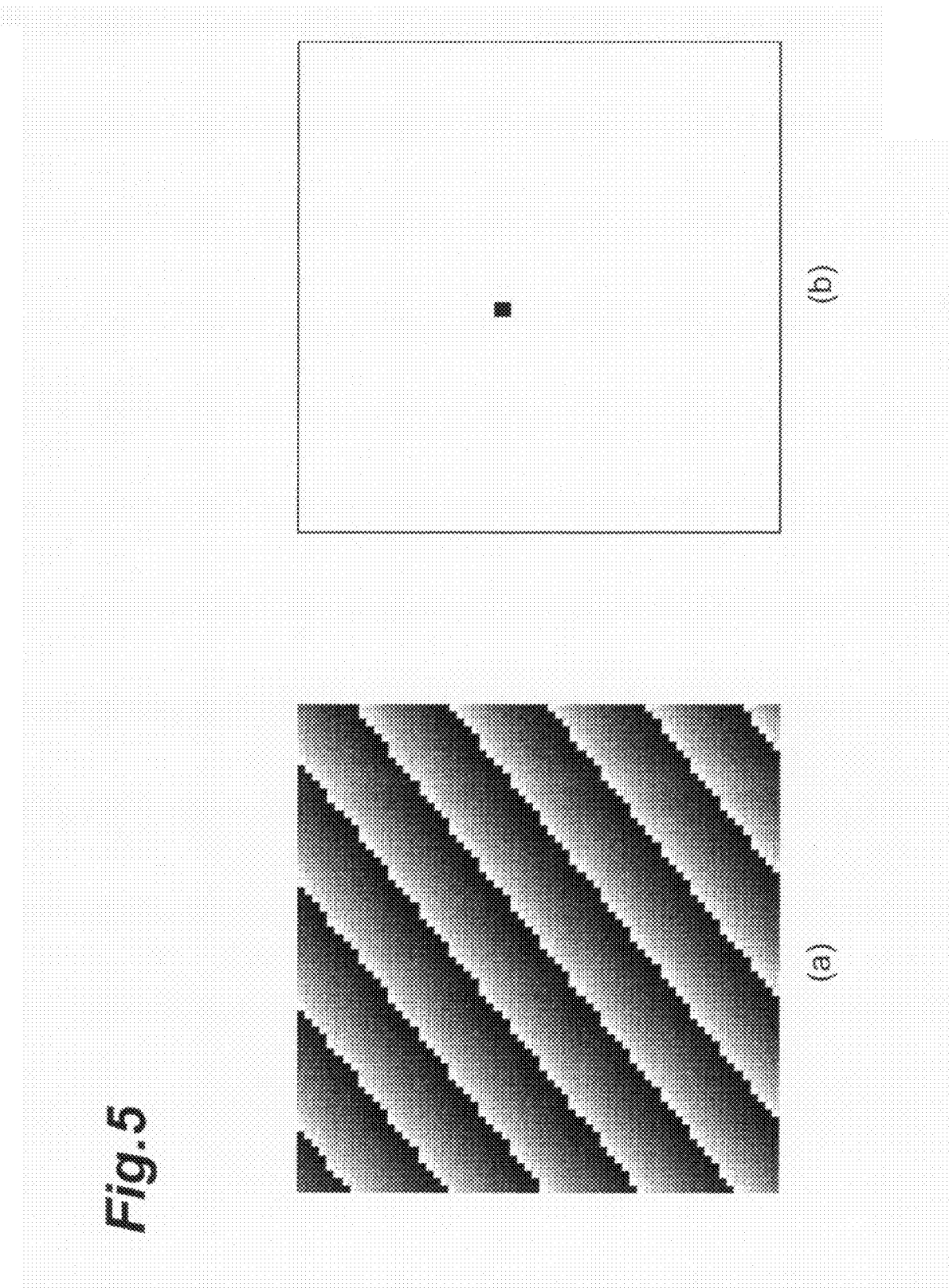
FIG. 5 are drawings showing a second example of spatial phase modulation of excitation light in the spatial light modulator 115.

In the second example shown in FIG. 5, a one-dimensional phase grating as shown in FIG. 5A is formed in the spatial light modulator 115, and according to this, one excitation light irradiation region shown in FIG. 5B is formed in the determined specimen 1. The position of the excitation light irradiation region to be formed in the determined specimen 1 is defined according to the period and orientation of the one-dimensional phase grating formed on the spatial light modulator 115, and is adjustable in the directions (x direction and y direction) perpendicular to the optical axis of the objective lens 101.

Figure 6:
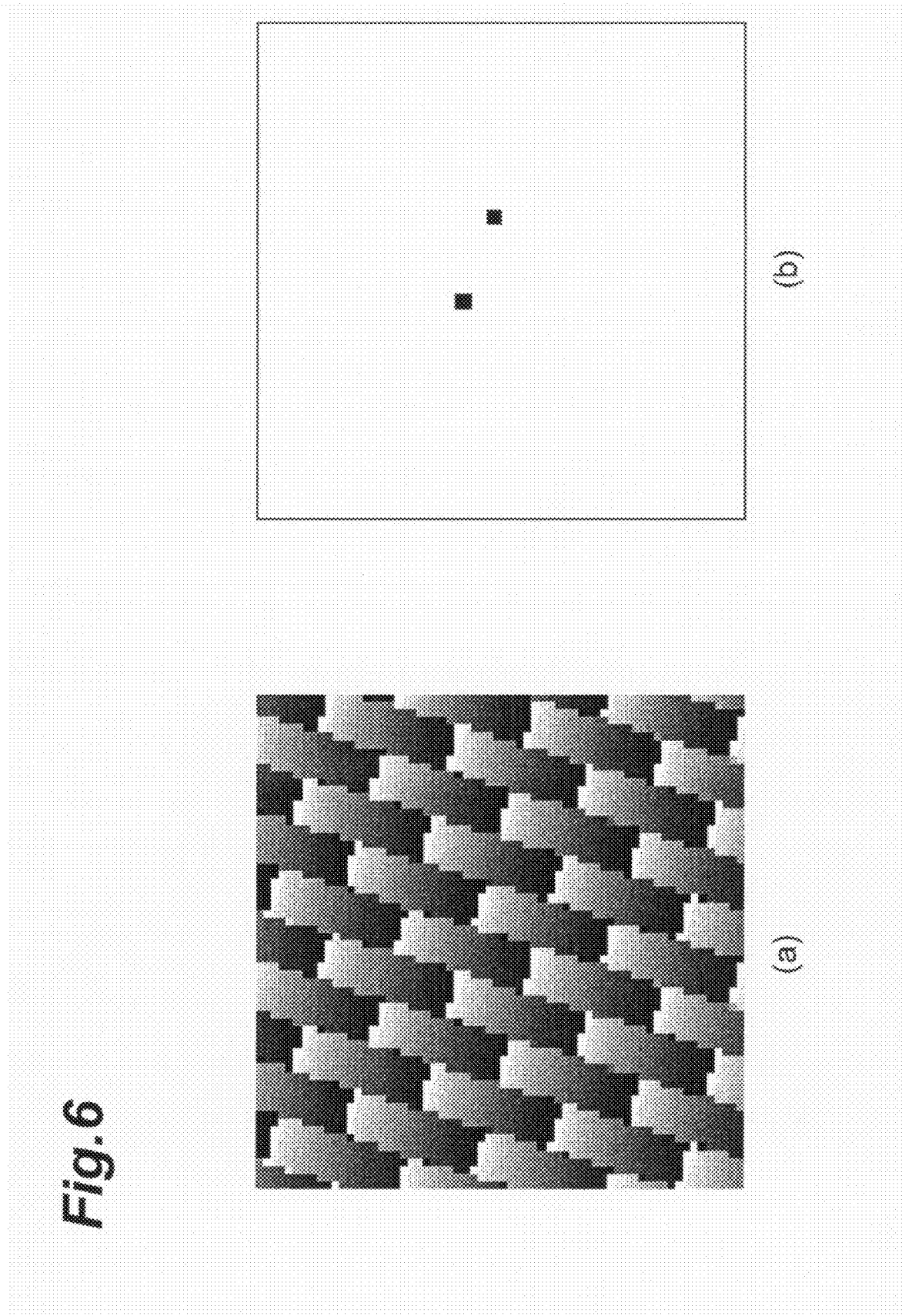
FIG. 6 are drawings showing a third example of spatial phase modulation of excitation light in the spatial light modulator 115.

In the third example shown in FIG. 6, a two-dimensional phase grating as shown in FIG. 6A is formed in the spatial light modulator 115, and according to this, two excitation light irradiation regions as shown in FIG. 6B are formed in the determined specimen 1. The positions of the respective excitation light irradiation regions to be formed in the determined specimen 1 are defined according to the orientations and periods of the two-dimensional phase grating to be formed on the spatial light modulator 115. In FIG. 6B, the excitation light intensity in the excitation light irradiation region at the left and the excitation light intensity in the excitation light irradiation region at the right are equal to each other.

Figure 7:
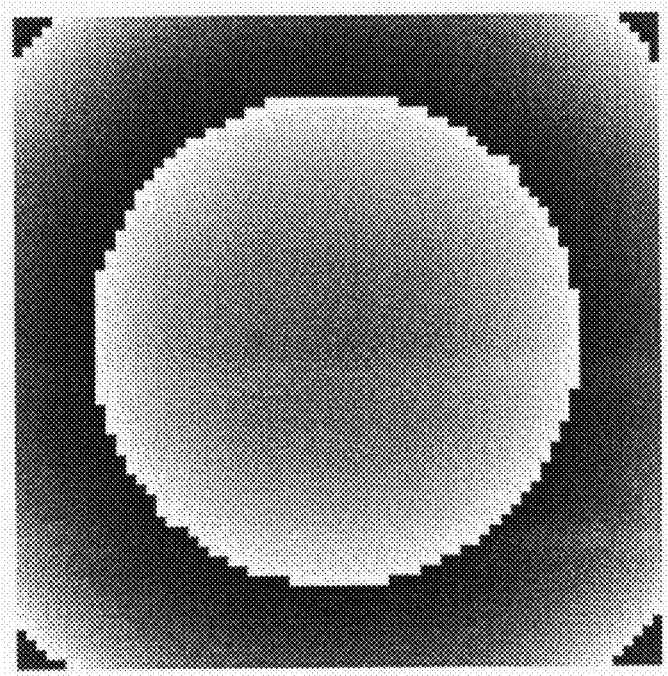
FIG. 7 is a drawing showing a fourth example of spatial phase modulation of excitation light in the spatial light modulator 115.

In the fourth example shown in FIG. 7, a spatial phase modulation pattern in which the phase gradually changes in a diameter direction around a principal ray incidence position is formed in the spatial light modulator 115. In this case, the spatial light modulator 115 acts like a refractive index distribution type lens. The position of an excitation light irradiation region to be formed in the determined specimen 1 is defined according to a rate of phase change in the diameter direction in the spatial light modulator 115, and is adjustable in a direction (z direction) parallel to the optical axis of the objective lens 101.

Figure 8:
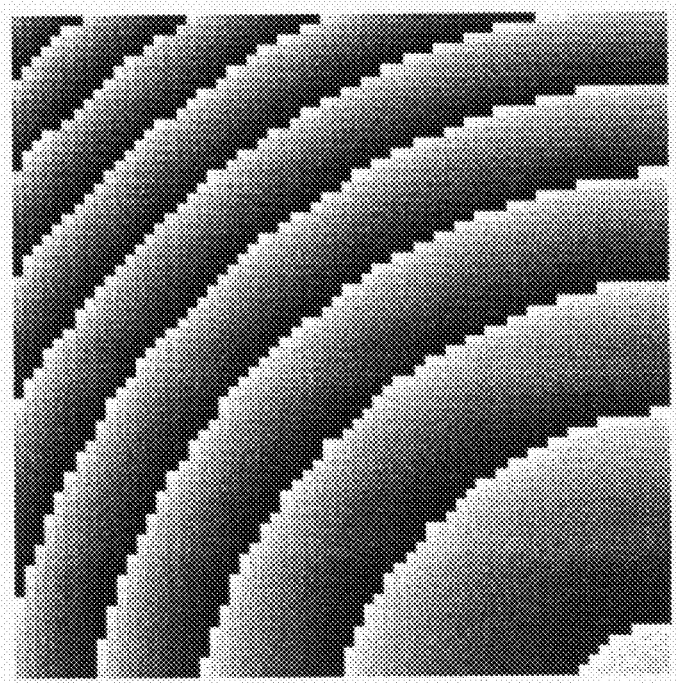
FIG. 8 is a drawing showing a fifth example of spatial phase modulation of excitation light in the spatial light modulator 115.

In the fifth example shown in FIG. 8, a spatial phase modulation pattern to be formed in the spatial light modulator 115 is obtained by combining the spatial phase modulation pattern shown in FIG. 5A and the spatial phase modulation pattern shown in FIG. 7. In this case, the position of an excitation light irradiation region to be formed in the determined specimen 1 is adjustable in the directions (x direction and y direction) perpendicular to the optical axis of the objective lens 101 and adjustable in the direction (z direction) parallel to the optical axis of the objective lens 101.

Figure 9:
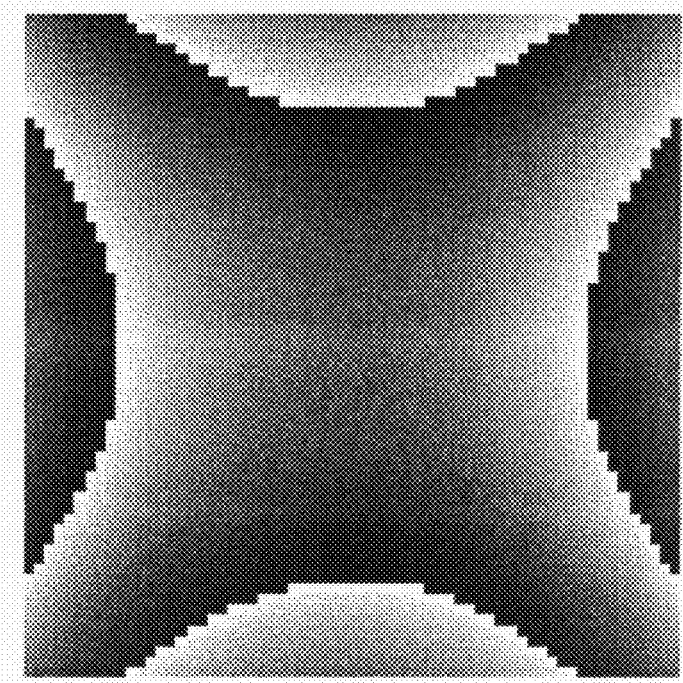
FIG. 9 is a drawing showing a sixth example of spatial phase modulation of excitation light in the spatial light modulator 115.

In the sixth example shown in FIG. 9, a spatial phase modulation pattern to be formed in the spatial light modulator 115 can correct astigmatism of the optical system from the spatial light modulator 115 to the determined specimen 1.

As seen in these FIG. 4 through FIG. 9, according to the spatial phase modulation pattern of excitation light in the spatial light modulator 115, the number, positions, and excitation light intensities of excitation light irradiation regions to be formed in the determined specimen 1 can be adjusted, and aberrations (including not only astigmatism but also chromatic aberration and spherical aberration, etc.) of the excitation light irradiating optical system can be corrected. By forming a spatial light modulator by overlapping the spatial phase modulation pattern shown in FIG. 9 with another spatial phase modulation pattern, adjustment of the number, positions, and excitation light intensities of excitation light irradiation regions to be formed in the determined specimen 1 and correction of aberrations of the excitation light irradiating optical system are allowed at the same time.

Figure 10:
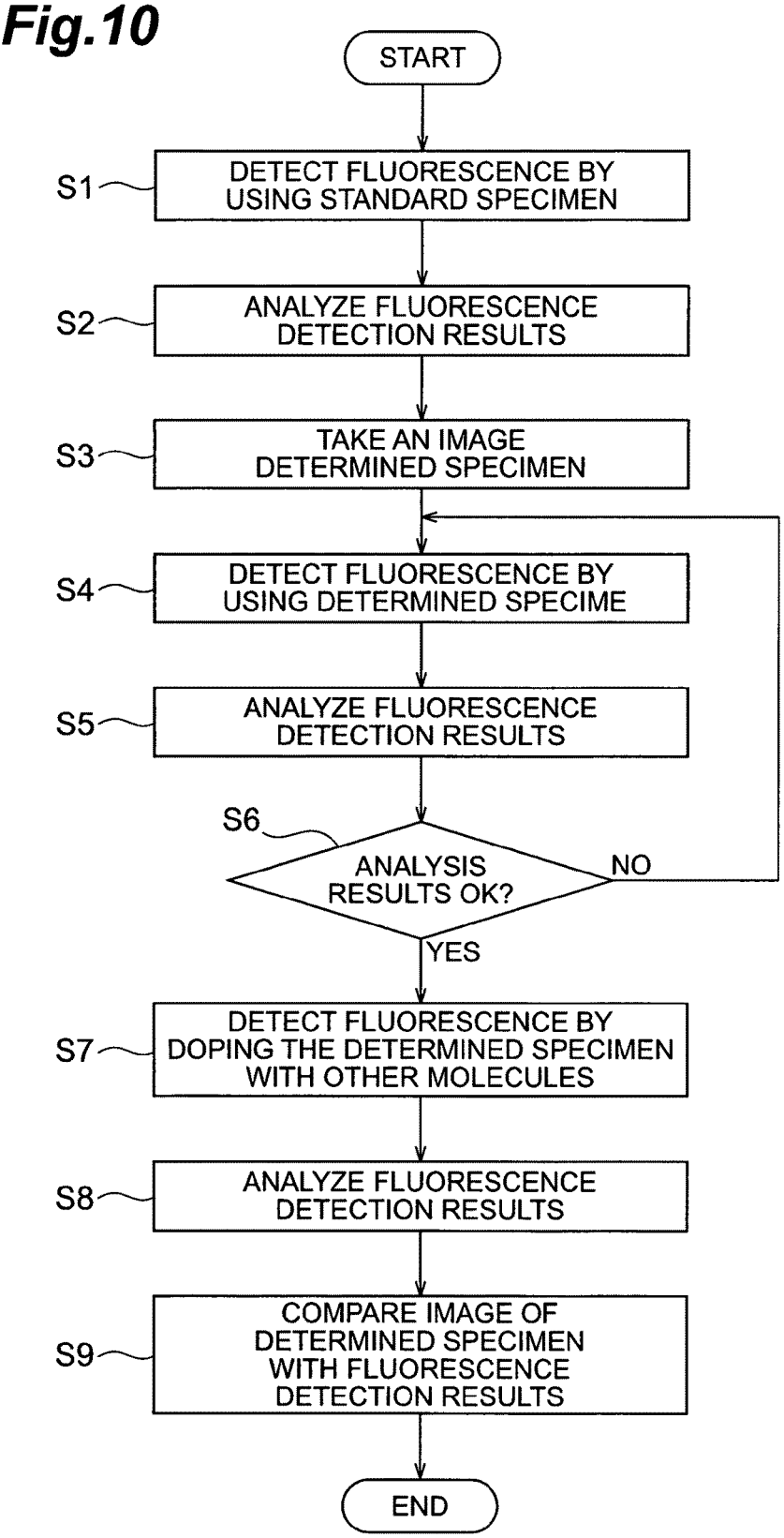
FIG. 10 is a flowchart showing procedures of fluorescence correlation spectroscopy using the fluorescence correlation spectroscopy analysis device 10 of the first embodiment.

Next, an example of fluorescence correlation spectroscopy using the fluorescence correlation spectroscopy analysis device 10 according to the first embodiment will be described. FIG. 10 is a flowchart showing procedures of fluorescence correlation spectroscopy using the fluorescence correlation spectroscopy analysis device 10 according to the first embodiment.

First, at Step S1, a standard specimen is placed instead of the determined specimen 1 on the transparent plate 2 and subjected to fluorescence detection. Herein, the standard specimen contains a fluorescent material whose molecular weight is known in a medium (buffer solution) whose viscosity is known. As the buffer solution, for example, water is used. As the fluorescent material, for example, green fluorescence protein (GFP) is used as it is, or Angiotensin or Biotin labeled by a fluorescent dye such as Rhodamin or Alexa, etc., is used.

In the state that such a standard specimen is placed on the transparent plate 2, excitation light (for example, a wavelength: 488 nanometers) is outputted from the laser light source 111. This excitation light is adjusted in intensity by the ND filter 112 and adjusted in a light beam diameter by the beam expander 113, reflected by the mirror 114, and made incident on the spatial light modulator 115. The excitation light that was made incident on the spatial light modulator 115 and spatially modulated is reflected by the dichroic mirror 102, and irradiated onto the standard specimen on the transparent plate 2 through the objective lens 101.

Fluorescence generated in the excitation light irradiation region is made incident on the spatial light modulator 133 through the objective lens 101, the dichroic mirror 102, the half mirror 105, the lens 131, and the band pass filter 132. Fluorescence made incident on a specific region of the fluorescence made incident on the spatial light modulator 133 is received by and its intensity is detected by the detector 134, and a change I(t) over time in detected intensity of the fluorescence is stored by the analyzer 12. At this time, the optical system from the excitation light irradiation region in the standard specimen to the spatial light modulator 133 forms an equivalent confocal optical system.

At the next Step S2, the analyzer 12 analyzes the change I(t) over time in fluorescence intensity detected at Step S1. That is, an autocorrelation function is calculated from this I(t) (the expression (1) above), and the calculated autocorrelation function is subjected to fitting by the autocorrelation function $G(\tau)$ of the following expression (2) in the case of supposing an ideal molecular motion model. In this expression (2), F indicates a ratio of a triplet state, and $\tau_{trip}$ indicates a triplet state attenuation time, N indicates average molecule counts of a fluorescent material in the excitation light irradiation region, M indicates a component identification number (M=1, 2, or 3), $y_i$ indicates a contribution ratio of the i-th component, and $\tau_{Di}$ indicates a translational diffusion time of the i-th component. S indicates a structural parameter to be defined from the radius w and length L of the excitation light irradiation region (see FIG. 3).

[Numerical expression 2]

$$G(\tau) = \frac{1 + \dfrac{F \cdot \exp\left(-\dfrac{\tau}{\tau_{trip}}\right)}{1-F}}{N} \left\{ \sum_{i=1}^{M} \frac{y_i}{\left(1 + \dfrac{\tau}{\tau_{Di}}\sqrt{\left(1 + \dfrac{\tau}{\tau_{Di}} \cdot \dfrac{1}{S^2}\right)}\right)} \right\} + 1 \quad (2a)$$

$$\sum_{i=1}^{M} y_i = 1 \quad (2b)$$

In this fitting, for example, the least square method is used, and based on an autocorrelation function obtained by actual determination, a parameter in the autocorrelation function in the case of supposing an ideal molecular motion model is defined. The parameter to be defined herein is a translational diffusion time $\tau_{Di}$ of the fluorescent material in the standard specimen or an average molecule counts N of the fluorescent material in the excitation light irradiation region. If the translational diffusion time $\tau_{Di}$ of the fluorescent material in the standard specimen is calculated, a fluorescence quantity per one fluorescence molecule is easily calculated from the fluorescence intensity detected by actual determination.

At the next Step S3, a determined specimen 1 to be determined is placed on the transparent plate 2 and taken an image. Herein, the determined specimen 1 is, for example, a cell, and includes an observation region 1A and an observation region 1B different from each other in refractive index or transmissivity (see FIG. 2). This determined specimen 1 is doped with the same fluorescent material as that doped in the standard specimen at Steps S1 and S2.

In such a state that this determined specimen 1 is placed on the transparent plate 2, when excitation light is outputted from the laser light source 111, the excitation light is adjusted in intensity by the ND filter 112 and adjusted in a light beam diameter by the beam expander 113, reflected by the mirror 114, and made incident on the spatial light modulator 115. The excitation light which was made incident on the spatial light modulator 115 and spatially modulated excitation light is reflected by the dichroic mirror 102 and irradiated onto the determined specimen 1 on the transparent plate 2 through the objective lens 101. At this time, spatial modulation of the excitation light in the spatial light modulator 115 changes over time, and on the determined specimen 1, spot-like excitation light is two-dimensionally scanned or linear excitation light is one-dimensionally scanned.

Fluorescence generated in the excitation light irradiation region in the determined specimen 1 is taken an image on an imaging surface of the CCD 153 through the objective lens 101, the dichroic mirror 102, the half mirror 105, the mirror 106, the lens 151, and the band pass filter 152. As described above, by scanning the irradiation of the excitation light onto the determined specimen 1, the determined specimen 1 is taken an image by the CCD 153. Then, the image of the determined specimen 1 is displayed on the display 13, and thereby, the observation region 1A and the observation region 1B in the determined specimen 1 can be clearly distinguished. When imaging the determined specimen 1, an illuminating light source or illuminating optical system exclusive for illuminating the determined specimen 1 may be used.

At the next Step S4, the determined specimen 1 is placed on the transparent plate 2, and fluorescence detection is performed in the same manner as in Step S1. Herein, in the observation regions 1A and 1B in the determined specimen 1, excitation light irradiation regions are formed, respectively. For example, the excitation light irradiation regions $P_1$ and $P_2$ are formed in the observation region 1A, and an excitation light irradiation region $P_3$ is formed in the observation region 1B (see FIG. 2). Then, changes I(t) over time in intensity of fluorescence detected in each of the excitation light irradiation regions $P_1$ though $P_3$ are stored in the analyzer 12.

At the next Step S5, changes I(t) over time in fluorescence intensity in the respective excitation light irradiation regions $P_1$ through $P_3$ detected at Step S4 are analyzed by the analyzer 12 in the same manner as in Step S2. Thereby, a translational diffusion time or average molecule counts of the fluorescent material are calculated for each of the excitation light irradiation regions $P_1$ through $P_3$.

At the next Step S6, it is judged whether the results obtained at Step S5 concerning the respective excitation light irradiation regions $P_1$ and $P_2$ in the observation region 1A are equivalent. If the results of these are different from each other, to adjust the intensities of excitation light to be irradiated onto the respective excitation light irradiation regions $P_1$ and $P_2$, the spatial modulation pattern of the excitation light by the spatial light modulator 15 is changed, and then Steps S4 and S5 are performed again. On the other hand, if the results of these are equivalent to each other, the process advances to the next Step S7.

At Step S7, the determined specimen 1 on the transparent plate 2 is doped with other molecules that can be specifically bonded to the fluorescent material that has already doped, and fluorescence detection is performed in the same manner as in Step S4. Herein, for example, when the fluorescent material that has already been doped is GFP, other molecules to be newly doped are of anti-GFP. When the fluorescent material that has already been doped is angiotensin labeled by a fluorescent dye, other molecules to be newly doped are of anti-angiotensin. When the fluorescent material that has already been doped is biotin labeled by a fluorescent dye, other molecules to be newly doped are of anti-biotin. Changes I(t) over time in intensity of fluorescence detected in the respective excitation light irradiation regions $P_1$ through $P_3$ are stored in the analyzer 12.

At the next Step S8, in the same manner as in Step S5, changes I(t) over time in fluorescence intensity in the respective excitation light irradiation regions $P_1$ through $P_3$ detected at Step S7 are analyzed by the analyzer 12. Thereby, a translational diffusion time or average molecule counts of the fluorescent material is calculated for each of the excitation light irradiation regions $P_1$ through $P_3$. A molecule AB formed by bonding the fluorescent material (molecule A) that has already been doped and another molecule (molecule B) newly doped has a greater molecular weight and slower Brownian motion than those of the molecule A, so that the translational diffusion constant of the molecule AB is great.

Therefore, by comparing the translational diffusion times of the fluorescent material obtained for the respective excitation light irradiation regions $P_1$ though $P_3$ with each other, the degrees of bonding between the molecule A and the molecule B in the observation region 1A and the observation region 1B are obtained. In each of the observation region 1A and observation region 1B, the detection ratio of the molecules A and the bonded molecules AB and dissociation constant (Kd value) are also calculated, and translational diffusion times of the molecules A and the bonded molecules AB are also calculated (refer to Japanese Published Unexamined Patent Application No. H11-326208).

At Steps S7 and S8, without newly doping the determined specimen 1 on the transparent plate 2 with other molecules, also when the fluorescent material that has already been doped in the determined specimen 1 is specifically bonded to other molecules existing in or produced in the determined specimen 1, interaction between the florescent material and other molecules can be analyzed. For example, when the fluorescent material that has already been doped is specifically sequenced nucleic acid labeled by a fluorescent dye, other molecules in the determined specimen 1 are molecules produced inside the cell as the determined specimen (nucleic acid or protein capable of being specifically bonded to the doped nucleic acid). When the molecular bonding is promoted or suppressed by an external stimulus, the interaction between molecules can also be determined in the same manner. The external stimulus referred to herein is, for example, an electrical stimulus, an magnetic stimulus, a chemical stimulus, a thermal stimulus, an optical stimulus, a stimulus due to radiation irradiation, or the like.

At the next Step S9, the image of the determined specimen taken an image at Step S3 and the results of fluorescence detection of the determined specimen 1 obtained at Step S8 are compared. FIGS. 11 show the image of the determined specimen 1 taken an image at Step S3 and the results of fluorescence detection of the determined specimen 1 obtained at Step S8. FIG. 11A shows only the image of the determined specimen 1 taken an image at Step S3, and FIG. 11B shows the image of the determined specimen 1 taken an image at Step S3 and the results of fluorescence detection (translational diffusion time or average molecule counts of the fluorescent material) in an overlapping manner. For example, as shown in this figure, the translational diffusion time is greater in, in the order of greatness with the greatest one first, region $1A_1$ close to the observation region 1B in the observation region 1A, region $1A_2$ surrounding the region $1A_1$ in the observation region 1A, region $1A_3$ surrounding the region $1A_2$ in the observation region 1A, and the remaining region $1A_4$ in the observation region 1A. From this indication, the action, etc., of protein inside the cell as the determined specimen 1 can be analyzed.

Thus, by successively changing the spatial modulation pattern of the excitation light in the spatial light modulator 115, distribution of the results of fluorescence detection of the determined specimen 1 in the field of the objective lens 101 can be obtained. At this time, the distribution of the results of fluorescence detection of the determined specimen 1 is obtained not only in the directions (x direction and y direction) perpendicular to the optical axis but also in the direction (z direction) parallel to the optical axis of the objective lens 101, so that three-dimensional distribution of the results of fluorescence detection of the determined specimen 1 in the field of the objective lens 101 is obtained.

Second Embodiment

Figure 12:
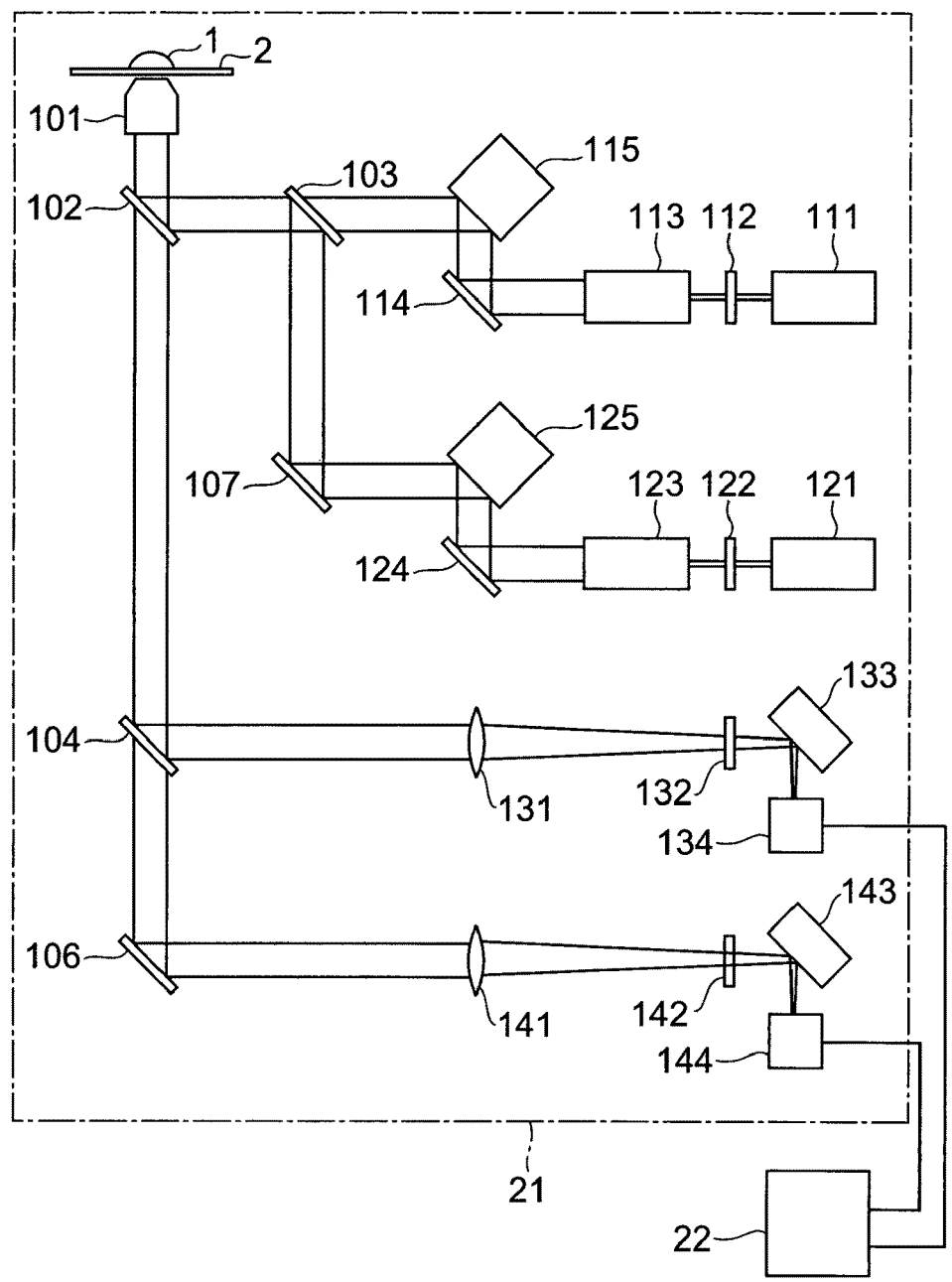
FIG. 12 is a construction diagram of a fluorescence correlation spectroscopy analysis device 20 according to a second embodiment.

Next, a second embodiment of the fluorescence microscope and the fluorescence correlation spectroscopy analysis device according to the invention will be described. FIG. 12 is a construction diagram of the fluorescence correlation spectroscopy analysis device 20 according to the second embodiment. The fluorescence correlation spectroscopy analysis device 20 shown in this figure includes a fluorescence microscope 21 and an analyzer 22, and detects fluorescence generated in a determined specimen 1 placed on a transparent plate 2 by irradiating the determined specimen 1 with excitation light. This fluorescence correlation spectroscopy analysis device 20 is preferably used especially for determining the determined specimen 1 by using the fluorescence cross correlation spectroscopy (FCCS).

The fluorescence microscope 21 includes an objective lens 101, a dichroic mirror 102, a dichroic mirror 103, a dichroic mirror 104, a mirror 106, a mirror 107, a laser light source 111, an ND filter 112, a beam expander 113, a mirror 114, a spatial light modulator 115, a laser light source 121, an ND filter 122, a beam expander 123, a mirror 124, a spatial light modulator 125, a lens 131, a band pass filter 132, a spatial light modulator 133, a detector 134, a lens 141, a band pass filter 142, a spatial light modulator 143, and a detector 144.

The optical system from the laser light source 111 and the laser light source 121 to the determined specimen 1 forms an excitation light irradiating optical system for irradiating the determined specimen 1 with excitation light outputted from the laser light sources 111 and 121. The optical system from the determined specimen 1 to the detector 134 and the detector 144 forms a fluorescence detecting optical system which guides fluorescence generated in the determined specimen 1 to the detectors 134 and 144. Also in this embodiment, it is preferable that an imaging optical system and imaging means for imaging the determined specimen 1 are provided, however, description of these is omitted.

In this embodiment, as an excitation light source for outputting excitation light, a laser light source 111 and a laser light source 121 which output excitation light beams different in wavelength from each other are provided. The first excitation light outputted from the laser light source 111 and the second excitation light outputted from the laser light source 121 have wavelengths capable of exciting the fluorescent material contained in the determined specimen 1.

The ND filter 112 adjusts the intensity of the first excitation light outputted from the laser light source 111 and then outputs it. The beam expander 113 receives an input of the first excitation light outputted from the ND filter 112, enlarges the light beam diameter of the first excitation light to an appropriate diameter and collimates it, and then outputs it. The spatial light modulator 115 receives an input of the first excitation light that was outputted from the beam expander 113 and reflected by the mirror 114, and spatially modulates the first excitation light and outputs the spatially modulated first excitation light.

The ND filter 122 adjusts the intensity of the second excitation light outputted from the laser light source 121 and outputs it. The beam expander 123 receives an input of the second excitation light outputted from the ND filter 122, enlarges the light beam diameter of the second excitation light and collimates it, and then outputs it. The spatial light modulator 125 receives an input of the second excitation light that was outputted from the beam expander 123 and reflected by the mirror 124, spatially modulates the second excitation light, and then outputs the spatially modulated second excitation light.

The spatial light modulators 115 and 125 are variable in its spatial modulation, and can set the number, positions, and shapes of regions to be irradiated with excitation light in the determined specimen 1 by irradiating the determined specimen 1 with spatially modulated excitation light via the subsequent optical system, and can solve the problem of unevenness of excitation light irradiation intensity and aberrations.

The spatial light modulators 115 and 125 may be a transmission type or a reflection type. The spatial light modulators 115 and 125 may be an amplitude modulation type or a phase modulation type, or may modulate both the amplitude and phase. However, in terms of use efficiency of excitation light, the spatial light modulators 115 and 125 are preferably a phase modulation type. For example, as the spatial light modulators 115 and 125, one including micro pixels containing liquid crystals two-dimensionally aligned on a plane is used.

The dichroic mirror 103 transmits the first excitation light outputted from the spatial light modulator 115, and reflects the second excitation light that was outputted from the spatial light modulator 125 and reflected by the mirror 107, and outputs these first excitation light and second excitation light to the dichroic mirror 102 on the same light path.

The dichroic mirror 102 reflects the first excitation light and the second excitation light that reached from the dichroic mirror 103 and makes these incident on the objective lens 101, and transmits fluorescence outputted from the objective lens 101. The objective lens 101 receives an input of the first excitation light and the second excitation light reflected by the dichroic mirror 102 and irradiates these excitation lights onto predetermined regions (excitation light irradiation regions) in the determined specimen 1. The objective lens 101 receives inputs of fluorescence generated in the excitation light irradiation regions and outputs the fluorescence to the dichroic mirror 102.

The dichroic mirror 104 separates first fluorescence generated in the excitation light irradiation region in the determined specimen 1 irradiated with the first excitation light and second fluorescence generated in the excitation light irradiation region in the determined specimen 1 irradiated with the second excitation light from each other. The first fluorescence and the second fluorescence are different in wavelength from each other. That is, the dichroic mirror 104 receives an input of light that was outputted from the objective lens 101 and transmitted through the dichroic mirror 102, and selectively reflects the first fluorescence in the inputted light, and transmits the second fluorescence (and scatter components of the excitation light). On the mirror 106, light transmitted through the dichroic mirror 104 is made incident, and the mirror reflects the second fluorescence in the incident light and absorbs the scatter components of the excitation light.

On the lens 131, the first fluorescence reflected by the dichroic mirror 104 is made incident, and the lens forms an image of the first fluorescence generated in the excitation light irradiation region in the determined specimen 1 on the spatial light modulator 133 in conjunction with the objective lens 101. The band pass filter 132 is provided on the light path between the lens 131 and the spatial light modulator 133, and selectively transmits the first fluorescence and blocks scatter components of the excitation light. The spatial light modulator 133 serves as selective output means for selectively outputting the first fluorescence inputted in a specific region of the imaging surface of the first fluorescence taken an image by the objective lens 101 and the lens 131. The detector 134 detects the intensity of the first fluorescence that was outputted from the spatial light modulator 133 and reached.

On the lens 141, the second fluorescence reflected by the mirror 106 is made incident, and the lens forms an image of the second fluorescence generated in the excitation light irradiation region in the determined specimen 1 on the spatial light modulator 143 in conjunction with the objective lens 101. The band pass filter 142 is provided on the light path between the lens 141 and the spatial light modulator 143, and selectively transmits the second fluorescence and blocks scatter components of the excitation light. The spatial light modulator 143 serves as selective output means for selectively outputting the second fluorescence made incident on a specific region of the imaging surface of the second fluorescence taken an image by the objective lens 101 and the lens 141. The detector 144 detects the intensity of the second fluorescence that was outputted from the spatial light modulator 143 and reached.

It is also possible that masks with apertures are used instead of the spatial light modulators 133 and 143 and fluorescence images are positioned at the aperture positions (specific regions). However, it is preferable that the positions and shapes of the specific regions are variable, so that it is preferable that the spatial light modulators 133 and 143 can vary the number, positions, and shapes of specific regions to which the fluorescence is selectively outputted in the fluorescence imaging surfaces. Thereby, an equivalent confocal optical system can be realized.

The spatial light modulators 133 and 143 may be a transmission type or a reflection type. Furthermore, the spatial light modulators 133 and 143 may be an amplitude modulation type or a phase modulation type, or may modulate both the amplitude and phase. However, the spatial light modulators 133 and 143 in the detecting optical system do not need various condition controls in comparison with the spatial light modulators 115 and 125 in the excitation light irradiating optical system, so that they are preferably an intensity modulation type in terms of cost.

The analyzer 22 stores a change $I_1(t)$ over time in intensity of the first fluorescence detected by the detector 134 and stores a change $I_2(t)$ over time in intensity of the second fluorescence detected by the detector 144, and calculates a cross correlation function $G(\tau)$ from these $I_1(t)$ and $I_2(t)$ (following expression (3)). Based on this cross correlation function $G(\tau)$, interaction of the fluorescent material in the excitation light irradiation regions in the determined specimen 1 can be analyzed.

[Numerical expression 3]

$$G(\tau) = \frac{\langle I_1(t) \cdot I_2(t+\tau) \rangle}{\langle I_1(t) \rangle \cdot \langle I_2(t) \rangle} \quad (3)$$

This fluorescence correlation spectroscopy analysis device 20 operates as follows. When the first excitation light (for example, wavelength: 488 nanometers) is outputted from one laser light source 111, the first excitation light is adjusted in intensity by the ND filter 112, adjusted in a light beam diameter by the beam expander 113, reflected by the mirror 114, made incident on the spatial light modulator 115, and spatially modulated by the spatial light modulator 115. When the second excitation light (for example, wavelength: 633 nanometers) is outputted from the other laser light source 121, the second excitation light is adjusted in intensity by the ND filter 122, adjusted in a light beam diameter by the beam expander 123, reflected by the mirror 124, made incident on the spatial light modulator 125, and spatially modulated by the spatial light modulator 125.

The first excitation light spatially modulated by the spatial light modulator 115 and the second excitation light spatially modulated by the spatial light modulator 125 are brought together on the same light path by the dichroic mirror 103, and then reflected by the dichroic mirror 102, and irradiate the determined specimen 1 on the transparent plate 2 through the objective lens 101. The determined specimen 1 is doped with a first fluorescent material labeled by a fluorescent dye (for example, Alexa 488) which can be excited by the first excitation light and a second fluorescent material labeled by a fluorescent dye (for example Alexa 633) which can be excited by the second excitation light.

First fluorescence (wavelength: 530 nanometers) generated according to irradiation of the first excitation light in the excitation light irradiation region in the determined specimen 1 is made incident on the spatial light modulator 133 through the objective lens 101, the dichroic mirror 102, the dichroic mirror 104, the lens 131, and the band pass filter 132. The first fluorescence made incident on a specific region of the first fluorescence made incident on the spatial light modulator 133 is received by and the intensity thereof is detected by the detector 134, and a change $I_1(t)$ over time in detected intensity of the first fluorescence is stored in the analyzer 22. At this time, the optical system from the excitation light irradiation region in the determined specimen 1 to the spatial light modulator 133 forms an equivalent confocal optical system.

Second fluorescence (wavelength: 680 nanometers) generated according to irradiation of the second excitation light in the excitation light irradiation region in the determined specimen 1 is made incident on the spatial light modulator 143 through the objective lens 101, the dichroic mirror 102, the dichroic mirror 104, the mirror 106, the lens 141, and the band pass filter 142. The second fluorescence made incident on a specific region of the second fluorescence made incident on the spatial light modulator 143 is received by and its intensity is detected by the detector 144, and a change $I_2(t)$ over time in detected intensity of the second fluorescence is stored by the analyzer 22. At this time, the optical system from the excitation light irradiation region in the determined specimen 1 to the spatial light modulator 143 forms an equivalent confocal optical system.

Then, by the analyzer 22, a cross correlation function $G(\tau)$ is calculated from these $I_1(t)$ and $I_2(t)$, and the calculated cross correlation function $G(\tau)$ is subjected to fitting by a cross correlation function of an ideal molecular motion model. Thereby, interaction between the first fluorescent material and the second fluorescent material in the excitation light irradiation region in the determined specimen 1 can be analyzed.

As described above, also in the fluorescence correlation spectroscopy analysis device 20 according to this embodiment, similar to the fluorescence correlation spectroscopy analysis device 10 of the first embodiment, according to the spatial phase modulation patterns of excitation light in the spatial light modulators 115 and 125, the number, positions, and excitation light intensities of excitation light irradiation regions to be formed in the determined specimen 1 can be adjusted, and aberrations of the excitation light irradiating optical system can be corrected.

Additionally, in this fluorescence correlation spectroscopy analysis device 20, the excitation light irradiation region in the determined specimen 1 is irradiated with first excitation light and second excitation light that are different in wavelength from each other, the first fluorescent material present in the excitation light irradiation region is excited by the first excitation light and first fluorescence is generated from the first fluorescent material, and the second fluorescent material present in the excitation light irradiation region is excited by the second excitation light and second fluorescence is generated from the second fluorescent material. Then, by the fluorescence cross correlation spectroscopy (FCCS), the first fluorescence intensity $I_1(t)$ and the second fluorescence intensity $I_2(t)$ are detected by the confocal optical system, and interaction between the first fluorescent material and the second fluorescent material in the excitation light irradiation region can be analyzed.

With this fluorescence correlation spectroscopy analysis device 20, it is also possible that a first excitation light irradiation region in the determined specimen 1 is irradiated with first excitation light and first fluorescence is detected, and on the other hand, a second excitation light irradiation region different from the first excitation light irradiation region is irradiated with second excitation light and second fluorescence is detected. Then, by the fluorescence correlation spectroscopy (FCS), behaviors of the fluorescent materials can be individually determined in each of the first excitation light irradiation region and the second excitation light irradiation region that are at different positions.

INDUSTRIAL APPLICABILITY

The above-described fluorescence microscope and fluorescence correlation spectroscopy analysis device according to the invention are preferable as instruments for determining translational diffusion motion, etc., of fluorescent material in a determined specimen.

The invention claimed is:

1. A fluorescence microscope which irradiates a determined specimen with excitation light and detects fluorescence generated according to the irradiation, comprising:
    an excitation light source which outputs excitation light;
    an excitation light irradiating optical system which has a spatial light modulator for spatially modulating excitation light outputted from the excitation light source and irradiates the determined specimen with excitation light spatially modulated by the spatial light modulator;
    a fluorescence detecting optical system which receives fluorescence generated in a region irradiated with excitation light by the excitation light irradiating optical system and forms an image of the fluorescence, and has selective output means for selectively outputting fluorescence made incident on a specific region of the imaging surface;
    a detector which detects an intensity of fluorescence outputted from the selective output means;
    imaging means for imaging the determined specimen; and
    means for distinguishing observation regions from each other from an image detected by the imaging means and forming a plurality of excitation light irradiation regions in at least one observation region by controlling a spatial light modulation of excitation light, means for judging whether the measurement results of the respective excitation light irradiation regions in the observation region are equivalent, and means for adjusting the spatial modulation pattern of the excitation and controlling the spatial light modulator to adjust the intensities of excitation light based on an analysis of fluorescence intensity at a plurality of irradiation regions in an observation region,
    wherein the spatial light modulator included in the excitation light irradiating optical system is a phase modulation type spatial light modulator.

2. The fluorescence microscope according to claim 1, wherein the selective output means included in the fluorescence detecting optical system is a spatial light modulator.

3. The fluorescence microscope according to claim 2, wherein a spatial light modulator to be used as the selective output means is an intensity modulation type spatial light modulator.

4. A fluorescence correlation spectroscopy analysis device comprising:
    the fluorescence microscope according to claim 3, and
    an analyzer which calculates an autocorrelation function of a change over time in intensity detected by the detector of the fluorescence microscope.

5. A fluorescence correlation spectroscopy analysis device comprising:
    the fluorescence microscope according to claim 2, and
    an analyzer which calculates an autocorrelation function of a change over time in intensity detected by the detector of the fluorescence microscope.

6. The fluorescence microscope according to claim 1, wherein
    the excitation light source outputs first excitation light and second excitation light that are different in wavelength from each other,
    exclusive spatial light modulators are provided for the respective first excitation light and the second excitation light as the spatial light modulator of the excitation light irradiating optical system, and the excitation light irradiating optical system irradiates the determined specimen with the spatially modulated first excitation light and second excitation light in the same light path,
    the fluorescence detecting optical system has a separator which separates first fluorescence generated in a region irradiated with the first excitation light in the determined specimen and second fluorescence generated in a region irradiated with the second excitation light from each other, and has the selective output means separately for each of the first fluorescence and the second fluorescence; and
    the detector detects intensities of the first fluorescence and the second fluorescence outputted from the selective output means.

7. A fluorescence correlation spectroscopy analysis device comprising:
    the fluorescence microscope according to claim 6; and
    an analyzer which calculates a cross correlation function of changes over time in intensity of first fluorescence and the second fluorescence detected by the detector of the fluorescence microscope.

8. A fluorescence correlation spectroscopy analysis device comprising:
    fluorescence microscope according to claim 1, and
    an analyzer which calculates an autocorrelation function of a change over time in intensity detected by the detector of the fluorescence microscope.

9. A fluorescence correlation spectroscopy analysis device comprising:
    the fluorescence microscope according to claim 1, and
    an analyzer which calculates an autocorrelation function of a change over time in intensity detected by the detector of the fluorescence microscope.

10. A fluorescence correlation spectroscopy analysis device comprising:
    the fluorescence microscope according to claim 1, and
    an analyzer which calculates an autocorrelation function of a change over time in intensity detected by the detector of the fluorescence microscope.

* * * * *